United States Patent
Suzuki et al.

(10) Patent No.: US 9,548,185 B2
(45) Date of Patent: Jan. 17, 2017

(54) CROSS SECTION PROCESSING METHOD AND CROSS SECTION PROCESSING APPARATUS

(71) Applicant: HITACHI HIGH-TECH SCIENCE CORPORATION, Minato-ku, Tokyo (JP)

(72) Inventors: Hidekazu Suzuki, Tokyo (JP); Tatsuya Asahata, Tokyo (JP); Atsushi Uemoto, Tokyo (JP)

(73) Assignee: HITACHI HIGH-TECH SCIENCE CORPORATION (JP)

( * ) Notice: Subject to any disclaimer, the term of this patent is extended or adjusted under 35 U.S.C. 154(b) by 0 days.

(21) Appl. No.: 14/520,595

(22) Filed: Oct. 22, 2014

(65) Prior Publication Data
US 2015/0115156 A1  Apr. 30, 2015

(30) Foreign Application Priority Data

Oct. 24, 2013 (JP) ................................ 2013-221552
Oct. 10, 2014 (JP) ................................ 2014-209269

(51) Int. Cl.
H01J 37/26 (2006.01)
H01J 37/305 (2006.01)
G01N 1/32 (2006.01)
H01J 37/304 (2006.01)

(52) U.S. Cl.
CPC ............ *H01J 37/3056* (2013.01); *G01N 1/32* (2013.01); *H01J 37/304* (2013.01); *H01J 2237/31745* (2013.01)

(58) Field of Classification Search
USPC ....................................... 250/492.3
See application file for complete search history.

(56) References Cited

U.S. PATENT DOCUMENTS

| | | | |
|---|---|---|---|
| 6,723,650 B1 * | 4/2004 | Chang | H01J 37/26 216/37 |
| 7,232,767 B2 * | 6/2007 | George | H01J 37/321 257/E21.17 |
| 2004/0158409 A1 * | 8/2004 | Teshima | H01J 37/28 702/22 |

FOREIGN PATENT DOCUMENTS

JP  2008270073  11/2008

* cited by examiner

*Primary Examiner* — Phillip A Johnston
(74) *Attorney, Agent, or Firm* — Adams & Wilks

(57) ABSTRACT

A cross section processing method and a cross section processing apparatus are provided in which it is possible to form a flat cross section in a sample composed of a plurality of substances having different hardness by a focused ion beam. The etching of a processing area is performed while variably controlling the irradiation interval, the irradiation time, or the like of a focused ion beam based on cross section information of an SEM image obtained by the observation of a cross section. In this way, even if a sample is composed of a plurality of substances having different hardness, it is possible to form a flat observation surface with a uniform etching rate.

18 Claims, 6 Drawing Sheets

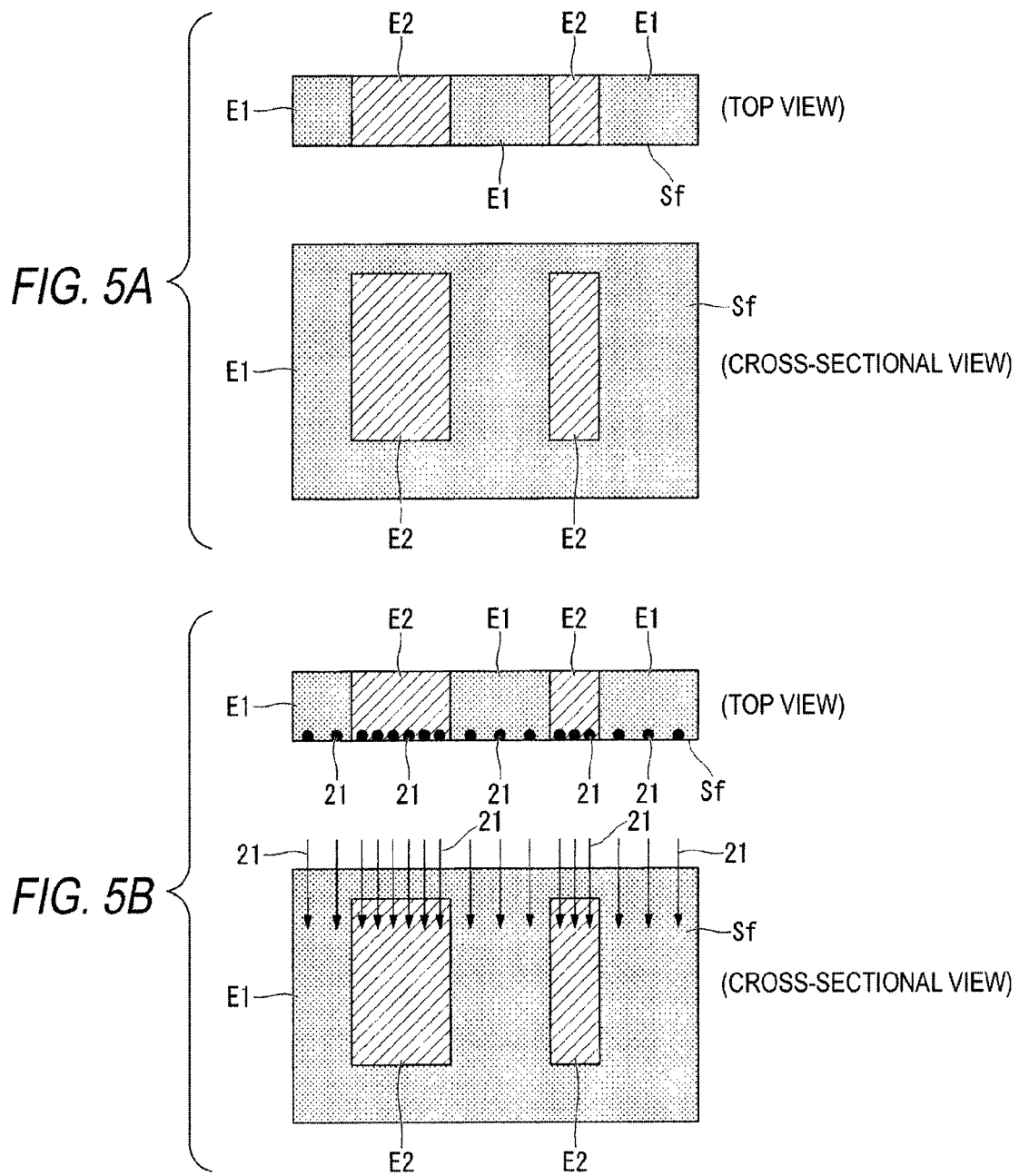

CROSS SECTION PROCESSING METHOD AND CROSS SECTION PROCESSING APPARATUS

This application claims priority from Japanese Patent Application No. 2013-221552 filed on Oct. 24, 2013 and Japanese Patent Application No. 2014-209269 filed on Oct. 10, 2014, the entire subject-matters of which are incorporated herein by reference.

BACKGROUND

1. Technical Field

The disclosure relates to a cross section processing method and a cross section processing apparatus for processing an observation surface of a sample which is observed by a microscope, by using a focused ion beam.

2. Description of the Related Art

For example, when observing and analyzing a sample such as a semiconductor device by a scanning electron microscope (SEM), a transmission electron microscope (TEM), an energy dispersive X-ray spectrometry (EDS), electron backscatter diffraction (EBSD), or the like, it is necessary to form a flat observation surface of the sample. In a case where an observation surface is not flat, it becomes difficult to obtain an accurate image of an observation surface (a cross section) or perform accurate component analysis.

In the past, in the formation of such an observation surface of the sample, a flat observation surface has been formed by polishing the sample or by the cleavage of the sample. However, in a case of polishing the sample, there is a concern that the sample may be contaminated by an abrasive or the like. Further, in a case of cleaving the sample, it is limited to a case where the sample is a crystalline substance.

For this reason, in recent years, as one of techniques of forming a flat observation surface of the sample, cross section formation processing (etching) by a focused ion beam (FIB) has been used (for example, JP-A-2008-270073). A method of forming an observation surface of the sample by using such a focused ion beam has the advantage of being able to accurately form a fine observation surface at an optional position of the sample, which is not present in other formation methods.

SUMMARY

In many samples which are observed and analyzed by the SEM, the TEM, the EDS, the EBSD, or the like, samples having a uniform composition are few, and many of them include a plurality of substances or a fine structure on the inside thereof. If the focused ion beam is emitted toward an objective observation surface at a uniform irradiation density and irradiation time with respect to such a sample composed of a plurality of substances, there is a problem in that the sample is not etched at a uniform etching rate. This is because the hardness varies according to the type of substance.

In a case where the sample is not etched at a uniform etching rate, for example, in a case where a substance having a high hardness and a low etching rate is locally present in the sample, so-called curtaining occurs in which a portion prior to the portion in which the substance is interrupted along an irradiation direction of the focused ion beam is also not removed because a substance having a high hardness acts as an etching mask. If such curtaining occurs, concaves and convexes may be formed on an observation surface, and as a result, it becomes difficult to observe and analyze the observation surface with a high degree of accuracy. For this reason, even in a sample composed of a plurality of substances having different hardness, a cross section processing method and a cross section processing apparatus, which form a flat observation surface by the irradiation of the focused ion beam, are required.

Therefore, illustrative aspects of the present invention provide a cross section processing method and a cross section processing apparatus which can form a flat cross section in a sample composed of a plurality of substances having different hardness by a focused ion beam.

In order to solve the above-described problem, according to some illustrative aspects of the present invention, the following cross section processing method and cross section processing apparatus are provided.

That is, according to one illustrative aspect of the present invention, there may be provided a cross section processing method of performing processing of a cross section of a sample by irradiating the sample with a focused ion beam, the method comprising: a cross section information obtaining process of obtaining cross section information of the sample; and a cross section processing process of forming an observation surface of the sample by performing etching of the cross section by irradiating the sample with the focused ion beam while varying an irradiation amount of the focused ion beam based on the obtained cross section information.

The varying the irradiation amount of the focused ion beam may comprise variably controlling at least one of an irradiation interval and irradiation time.

The cross section information may be contrast of the cross section or distribution of substances configuring the cross section.

The cross section information may be an etching rate map of the cross section created based on contrast of the cross section or distribution of substances configuring the cross section.

The cross section information obtaining process may be a process of obtaining an SEM image of the cross section of the sample.

The cross section information obtaining process may comprise performing EDS measurement or EBSD measurement of the cross section.

The cross section information may comprise information on an ion species of the focused ion beam measured by EDS measurement or EBSD measurement of the cross section.

The cross section processing process may be performed in a step-by-step manner until reaching an observation surface position having been set in advance, and the cross section information obtaining process may be performed at each step.

The cross section processing method may further comprise an irradiation condition generation process of generating irradiation conditions of the focused ion beam to be applied to the cross section based on the cross section information.

The cross section information obtaining process may comprise obtaining the cross section information based on EDS measurement or EBSD measurement of the cross section, and the method may further comprise forming a thin section of the sample by performing processing of a cross section of one side and a cross section on the other side of the sample based on the obtained cross section information.

The cross section information obtaining process may comprise obtaining the cross section information based on transmission electrons, reflected electrons, or secondary electrons, and the method may further comprise forming a thin section of the sample by performing processing of a cross section on one side and a cross section on the other side of the sample based on the obtained cross section information.

According to another illustrative aspect of the present invention, there may be provided a cross section processing apparatus comprising: a sample stage configured to place a sample thereon; a focused ion beam column configured to irradiate the sample with a focused ion beam; an electron beam column configured to irradiate the sample with an electron beam; a secondary electron detector configured to detect secondary electrons which are generated from the sample; and a control section configured to control the cross section processing apparatus to perform: a cross section information obtaining process of obtaining cross section information of the sample; and a cross section processing process of forming an observation surface of the sample by performing etching of the cross section by irradiating the sample with the focused ion beam while varying an irradiation amount of the focused ion beam, based on the obtained cross section information.

According to the illustrative aspects of the present invention, the etching of a processing area is performed while varying the irradiation amount of the focused ion beam based on cross section information obtained by the observation of a cross section of the sample. In this way, even if the sample is composed of a plurality of substances having different hardness, it is possible to form a flat cross section (observation surface) with a uniform etching rate.

BRIEF DESCRIPTION OF THE DRAWINGS

FIGS. 5A and 5B are explanatory diagrams showing an example of variable control of an FIB during etching of a sample.

DETAILED DESCRIPTION

Hereinafter, a cross section processing method and a cross section processing apparatus according to the present invention will be described with reference to the drawings. Incidentally, each embodiment shown below is for specifically describing the gist of the invention for better understanding thereof and does not limit the present invention unless otherwise specified. Further, the drawings which are used in the following description sometimes show a portion which is a main section in an enlarged manner for convenience sake in order to make the features of the present invention easy to understand, and the dimension, the ratio, or the like of each constituent element may not necessarily be the same in reality.

(Cross Section Processing Apparatus)

Figure 1:
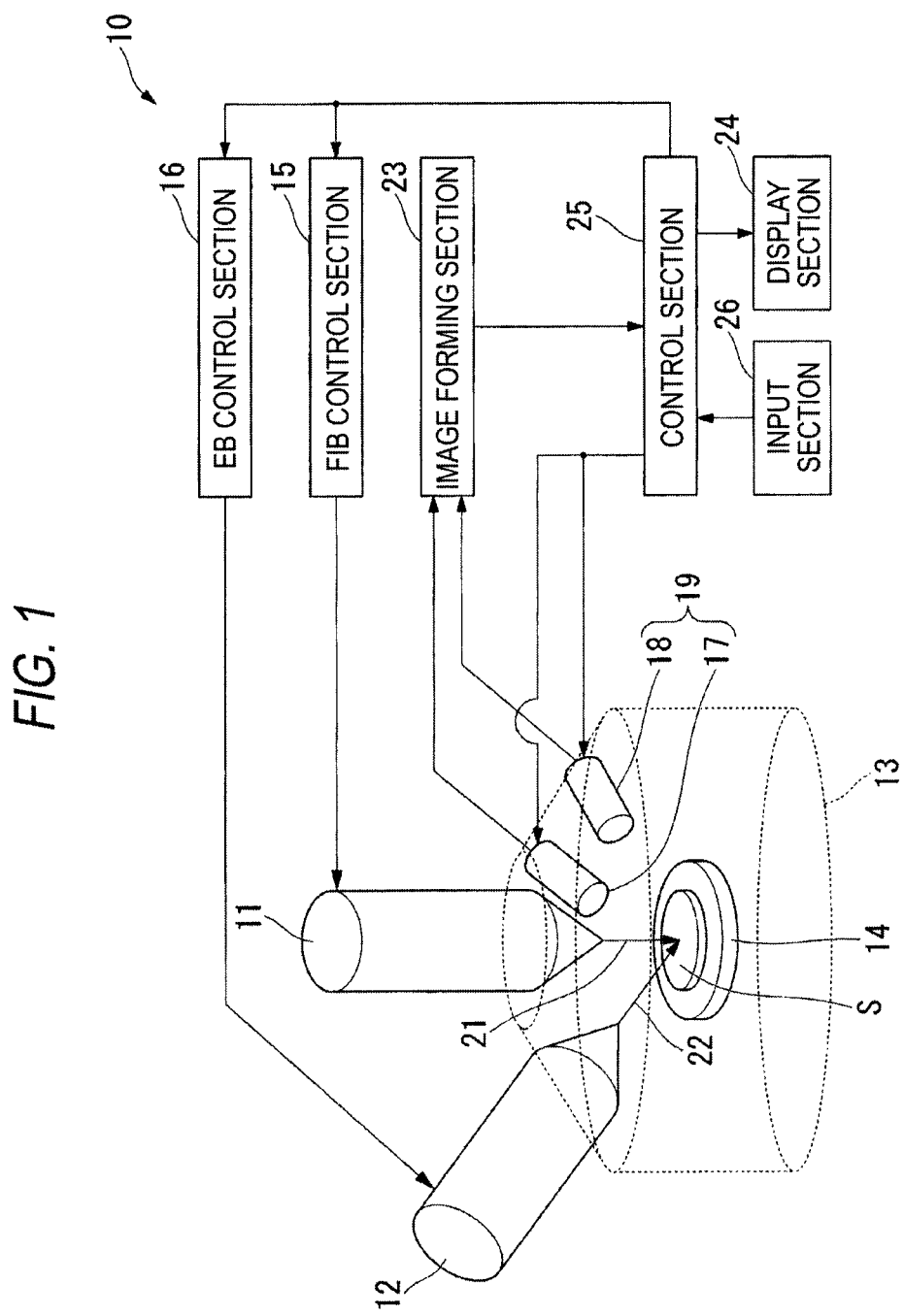
FIG. 1 is a schematic configuration diagram showing a cross section processing apparatus according to the present invention.

FIG. 1 is a schematic configuration diagram showing a cross section processing apparatus.

A cross section processing apparatus 10 according to the present invention is provided with a focused ion beam (FIB) column 11, an electron beam (EB) column 12, and a sample chamber 13. The focused ion beam column 11 and the electron beam column 12 are disposed so as to aim a focused ion beam (FIB) and an electron beam (EB) toward a sample S that is accommodated in the sample chamber 13 and is placed on a stage (a sample stage) 14. The stage 14 is configured to move and tilt in each of X, Y, and Z directions, whereby it is possible to adjust the sample S in an optional direction.

The cross section processing apparatus 10 is further provided with a focused ion beam (FIB) control section 15 and an electron beam (EB) control section 16. The focused ion beam control section 15 is configured to control the focused ion beam column 11 so as to emit a focused ion beam at an optional current value and at an optional timing. The electron beam control section 16 is configured to control the electron beam column 12 so as to emit an electron beam at an optional timing.

The cross section processing apparatus 10 is further provided with cross section information obtaining means 19. As the cross section information obtaining means 19, a secondary electron detector which detects secondary electrons generated from the sample S when the sample S is irradiated with the electron beam (EB), a reflected electron detector which detects reflected electrons reflected by the sample S when the sample S is irradiated with the electron beam (EB), a transmission electron detector which detects transmission electrons transmitted through the sample S when the sample S is irradiated with the electron beam (EB), an EDS detector which detects X-rays generated from the sample S when the sample S is irradiated with the electron beam (EB), an EBSD detector which detects an EBSD pattern due to electron backscatter diffraction generated in the sample S when the sample S is irradiated with the electron beam (EB), or the like can be used. As the cross section information obtaining means 19, the secondary electron detector, the reflected electron detector, the transmission electron detector, the EDS detector, or the like can be provided alone or in any combination.

In this embodiment, an example will be described in which among the secondary electron detector, the reflected electron detector, the transmission electron detector, the EDS detector, and the EBSD detector, a secondary electron detector 17 and an EDS detector 18 are provided as the cross section information obtaining means 19. However, the present invention is not limited thereto. Incidentally, in a case where the reflected electron detector is provided as the cross section information obtaining means 19, the reflected electron detector is formed inside the electron beam column 12.

The secondary electron detector 17 detects secondary electrons generated from the sample S by irradiating the sample S with a focused ion beam 21 or an electron beam 22. It is possible to obtain an SEM image of the sample S by such secondary electrons. Further, the EDS detector 18 detects X-rays generated from the sample S by irradiating the sample S with the electron beam 22. The X-rays generated from the sample S include a characteristic X-ray specific to each substance configuring the sample S, so that it is possible to identify the substance configuring the sample S by the characteristic X-ray.

Incidentally, a configuration in which the EBSD detector is further provided is also preferable. In the EBSD detector, if a crystalline material is irradiated with an electron beam, a diffraction pattern, that is, an EBSD pattern, is observed by electron backscatter diffraction occurring in the surface of the sample S and information about a crystal system or a crystal orientation of the sample S is obtained. By measuring and analyzing such an EBSD pattern, it is possible to obtain information about the distribution of a crystal system or a crystal orientation of a micro-region of the sample S, and thus it is possible to identify the substance configuring the sample S.

The cross section processing apparatus 10 is provided with an image forming section 23 which forms a cross section image of the sample S, and a display section 24 which displays the cross section image. The image forming section 23 forms the SEM image based on a signal of the secondary electrons detected by the secondary electron detector 17. The display section 24 displays the SEM image obtained in the image forming section 23. The display section 24 may be configured by, for example, a display device.

Further, the image forming section 23 forms an EDS map from a scanning signal of the electron beam 22 and a signal of the characteristic X-ray detected by the EDS detector 18. The display section 24 displays the EDS map obtained in the image forming section 23. Incidentally, the EDS map is for identifying the substance of the sample S at each electron beam irradiation point from the energy of the detected characteristic X-ray and showing the distribution of the substances of an irradiated area of the electron beam 22.

The cross section processing apparatus 10 is further provided with a control section 25 and an input section 26. An operator inputs various control conditions of the cross section processing apparatus 10 through the input section 26. The input section 26 transmits the input information to the control section 25. The control section 25 outputs control signals to the focused ion beam control section 15, the electron beam control section 16, and the image forming section 23 and controls an operation of the entirety of the cross section processing apparatus 10.

Figure 2:
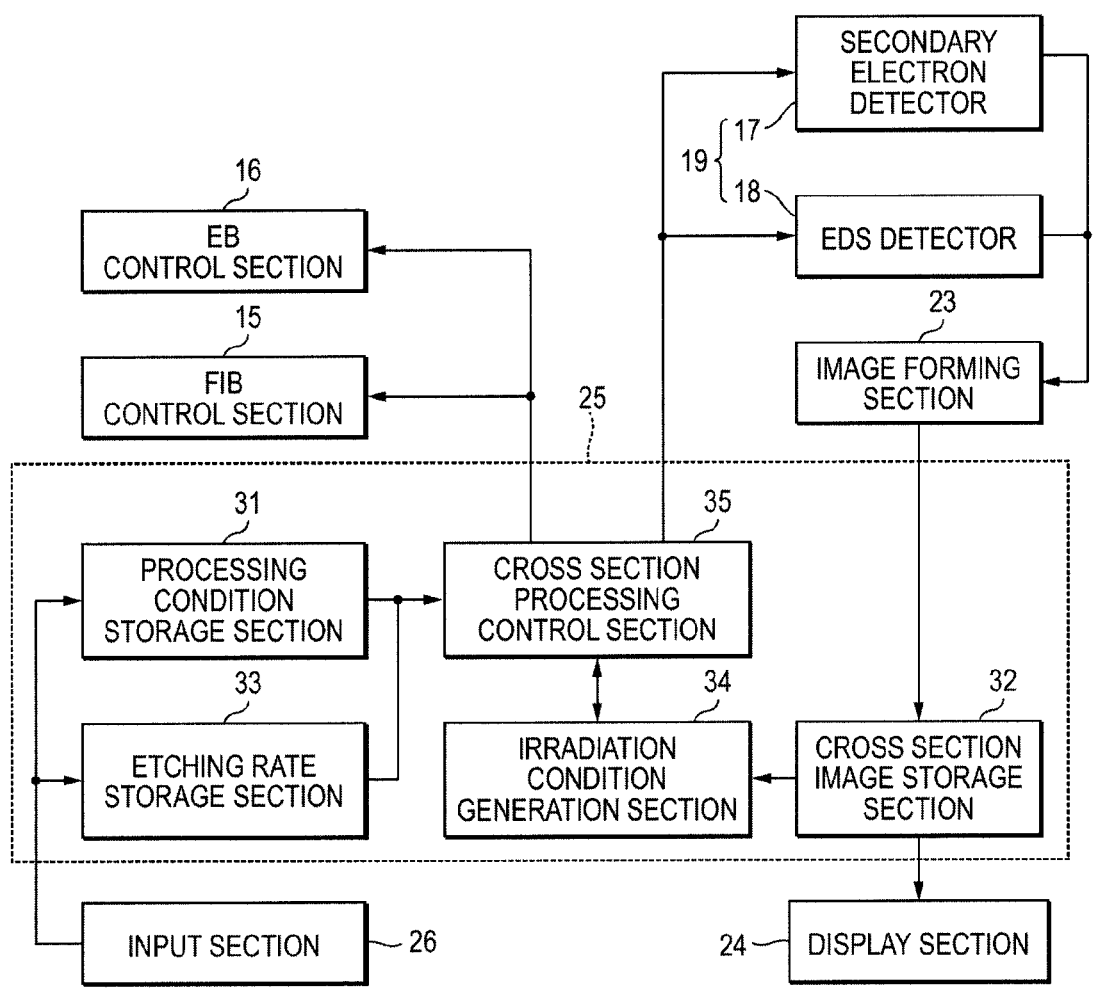
FIG. 2 is a schematic configuration diagram showing the configuration of a control section of the cross section processing apparatus.

FIG. 2 is a schematic configuration diagram showing the configuration of a control section of the cross section processing apparatus.

The control section 25 is provided with a processing condition storage section 31, a cross section image storage section 32, an etching rate storage section 33, an irradiation condition generation section 34, and a cross section processing control section 35.

The processing condition storage section 31 stores an irradiation interval or irradiation time of the focused ion beam according to an etching rate. Such data is referred to by the irradiation condition generation section 34 (which will be described later) at the time of the generation of the irradiation conditions of the focused ion beam 21.

The cross section image storage section 32 stores the SEM image of the cross section of the sample S formed by the image forming section 23. Such an SEM image is referred to by the irradiation condition generation section 34 (which will be described later) at the time of the generation of the control procedure of the focused ion beam 21.

Incidentally, in a case where the EDS detector 18 is provided as the cross section information obtaining means 19, the EDS map may also be stored in the cross section image storage section 32.

The etching rate storage section 33 stores a reference table of the etching rate (the ratio of a processing amount to an irradiation amount) for each material.

Incidentally, in a case where the EDS detector 18 is provided as the cross section information obtaining means 19, the etching rate storage section 33 may store a reference table of the etching rate according to the material identified by the EDS map. Further, in a configuration in which the EBSD detector is provided as the cross section information obtaining means 19, the etching rate storage section 33 may store a reference table of the etching rate according to an EBSD map.

The irradiation condition generation section 34 makes an etching rate map representing an area for each appropriate etching rate according to the material in the cross section of the sample S in a plane, from the brightness or the shading of the SEM image by reading the SEM image of the cross section of the sample S from the cross section image storage section 32 and by referring to the etching rate storage section 33.

Incidentally, in a case where the EDS detector 18 is provided as the cross section information obtaining means 19, the irradiation condition generation section 34 makes an etching rate map of the cross section of the sample S by reading the EDS map of the cross section of the sample S from the cross section image storage section 32 and by referring to the etching rate storage section 33. With respect to the etching rate map, at least one of the etching rate map based on the SEM image and the etching rate map based on the EDS map may be created. If plural kinds of etching rate maps are created, the accuracy of the etching rate map can be improved.

The irradiation condition generation section 34 generates the irradiation conditions of the focused ion beam necessary to uniformly etch the entire cross section of the sample S by referring to the irradiation interval (the distance between irradiation points) and the irradiation time (residence time of the focused ion beam) of the focused ion beam according to an etching rate from the processing condition storage section 31. Such irradiation conditions represent the irradiation interval and the irradiation time of the focused ion beam necessary for etching according to the hardness for each micro-region of the cross section of the sample S.

Incidentally, if the irradiation intensity of the focused ion beam is constant, the irradiation condition may be a condition representing the irradiation time. If the irradiation time of the focused ion beam is constant, the irradiation condition may be a condition representing the irradiation interval. The irradiation condition may be a condition representing the control of both the irradiation interval and the irradiation time.

The cross section processing control section 35 outputs information on the beam irradiation amount of the focused ion beam to the focused ion beam control section 15 based on the control procedure generated in the irradiation condition generation section 34.

(Outline of Cross Section Processing Method)

A cross section processing method according to the present invention using the cross section processing apparatus having the above-described configuration will be described. Here, a case of forming a thin sample which includes an observation surface set at an optional position of a semiconductor wafer is taken as an example of the cross section processing method according to the present invention. Such a thin sample is used for transmission observation by, for example, a TEM, and high flatness is required for the observation surface of the sample.

Figure 3A:
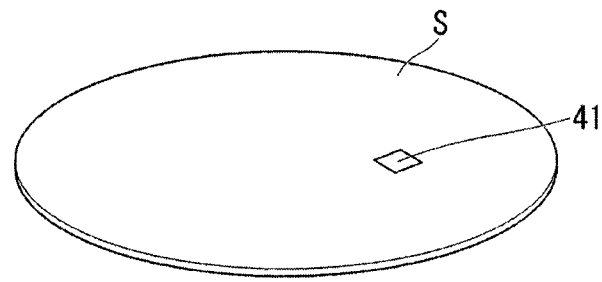
FIGS. 3A to 3D are explanatory diagrams showing a state of performing cross section processing of a semiconductor wafer.
Figure 3B:
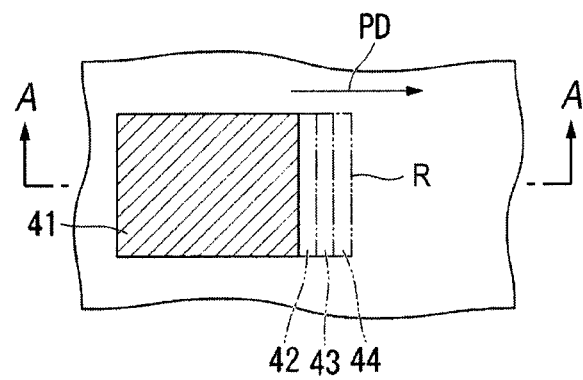
Figure 3C:
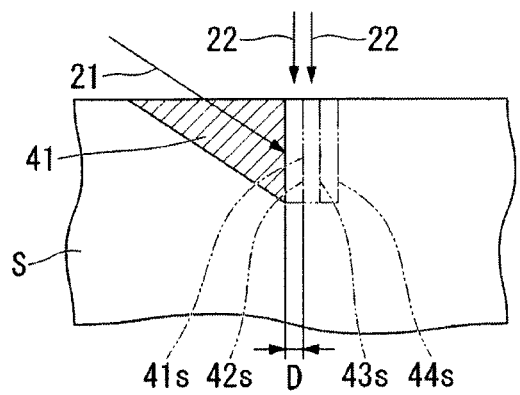

FIGS. 3A to 3D are explanatory diagrams showing a state of performing cross section processing of a semiconductor wafer. FIG. 3A shows a processing groove in the semiconductor wafer. FIG. 3B is an enlarged view showing the periphery of the processing groove. FIG. 3C is a cross-sectional view along line A-A of FIG. 3B.

The sample (the semiconductor wafer) S has a minute device structure on the inside thereof. In cross section processing observation, a cross section observation image of a desired observation target such as a device structure or a defect of the inside of the sample S is obtained and analyzed.

First, a position which is desired to observe a cross section in the sample (the semiconductor wafer) S is set as a formation planned position R of the observation surface. Then, the irradiation of the focused ion beam 21 is applied to the vicinity of the formation planned position R, thereby forming a processing groove 41 by etching, and the processing groove 41 is extended toward the formation planned position R. Incidentally, in the following description, a direction in which the processing groove 41 is extended toward the formation planned position R will be referred to as a processing direction PD.

As the processing groove 41 formed in the sample, a slope shape, in which a depth from the surface of the sample S gradually increases as it advances in the processing direction PD, is formed in advance so that a formed cross section 41s can be irradiated with the electron beam 22. Then, the processing groove 41 is extended in a step-by-step manner from the cross section 41s in the order of sliced processing areas 42, 43, and 44 along the processing direction PD. Finally, an observation surface 44s which is a cross section along a thickness direction of the formation planned position R is exposed.

Further, the electron beam 22 is emitted toward a rectangular cross section along a thickness direction of the sample S exposed by the processing, each time the processing of the processing areas 42 and 43 is completed, and an SEM observation image based on secondary electrons is obtained. Incidentally, the SEM observation image may be a reflected electron image based on reflected electrons. Further, instead of the SEM observation image, an EDS map or an EBSD map by the detection of the characteristic X-ray may be obtained. Alternatively, both the SEM observation image and the EDS map or the EBSD map may also be obtained.

The SEM observation images of cross sections 42s and 43s respectively obtained at the processing areas 42 and 43 are reflected in the variable control of the irradiation interval and the irradiation time of the focused ion beam 21 when etching the next processing area.

As described above, the SEM observation image of the cross section 42s is obtained by etching the processing area 42 with the focused ion beam 21 and irradiating the exposed cross section 42s with the electron beam 22. Next, when etching the processing area 43 with the focused ion beam 21, the cross section 43s is exposed by performing etching while variably controlling the irradiation interval or the irradiation time of the focused ion beam 21 based on the SEM observation image of the cross section 42s. In the same manner, when etching the processing area 44 with the focused ion beam 21, the observation surface (a cross section) 44s is exposed by performing etching while variably controlling the irradiation interval or the irradiation time of the focused ion beam 21 based on the SEM observation image of the cross section 43s.

Incidentally, in each cross section 42s, a configuration is also acceptable in which the cross section 43s is exposed by performing the etching while variably controlling the irradiation interval or the irradiation time of the focused ion beam 21 based on the EDS map or the EBSD map, instead of the SEM observation image or along with the SEM observation image.

Figure 3D:
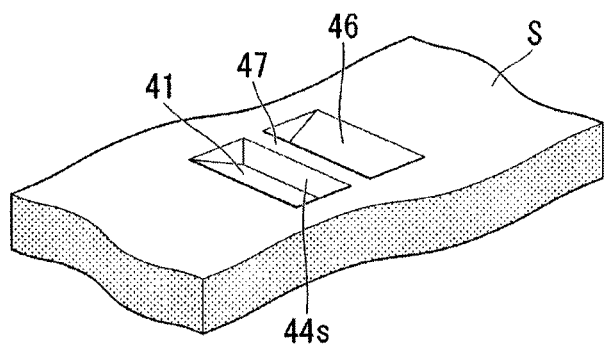

As shown in FIG. 3D, when forming the thin sample, after the observation surface (the cross section) 44s is formed, a processing groove 46 is formed toward the observation surface (the cross section) 44s from the vicinity of the opposite side to the observation surface (the cross section) 44s in the same manner as in the processes described above. According thereto, it is possible to obtain a thin section 47 having a final finish thickness of less than or equal to 200 nm and including the observation surface (the cross section) 44s.

(Embodiment of Cross Section Processing Method)

Next, the processing procedure will be described in more detail with reference to FIGS. 1 to 4 based on the outline of the above-described cross section processing method.

Figure 4:
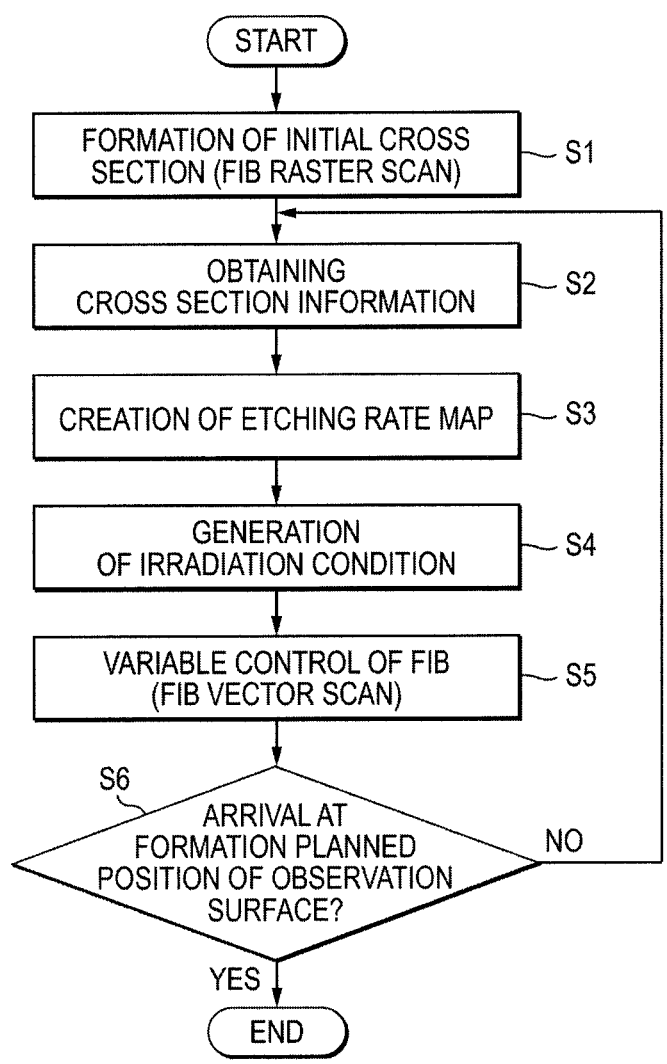
FIG. 4 is a flowchart showing the procedure of a cross section processing method.

FIG. 4 is a flowchart showing the cross section processing method according to the present invention.

First, the processing groove 41 having a slope shape is formed by etching by applying the focused ion beam 21 to the vicinity of the formation planned position R that has been set in advance. Subsequently, the etching of the processing area 42 (S1: initial cross section formation) is performed at a slice interval D toward the processing direction PD. The processing groove 41 having a slope shape and the processing area 42 may be formed by, for example, raster scan to uniformly emit the focused ion beam 21.

Next, the irradiation of the electron beam 22 is applied to the cross section 42s formed by slicing, and thus the image forming section 23 forms the SEM image of the cross section 42s based on secondary electrons generated from the sample S (S2: cross section information obtaining process). Then, the SEM image of the cross section 42s is stored in the cross section image storage section 32.

Incidentally, in a case where the EDS detector 18 is provided as the cross section information obtaining means 19, X-rays which are generated due to the irradiation of the electron beam 22 are further detected by the EDS detector 18. At this time, the specific X-rays of silicon, oxygen, aluminum, copper, and the like which are substances configuring a device from the sample S, which is a semiconductor wafer, are detected. The image forming section 23 forms the EDS map which is the distribution of substances of the irradiated area of the electron beam 21, based on the irradiation position of the electron beam 21 and the detected specific X-rays. Such an EDS map may be stored in the cross section image storage section 32.

Next, the irradiation conditions of the focused ion beam 21 when etching the processing area 43 are generated. First, the irradiation condition generation section 34 reads the SEM image of the cross section of the sample S formed by the image forming section 23 from the cross section image storage section 32. Next, the reference table linking the brightness or the shading of the SEM image and the etching rate together is referred to from the etching rate storage section 33.

Incidentally, in a case where the EDS detector 18 is provided as the cross section information obtaining means 19, the EDS map of the sample S formed by the image forming section 23 may be read from the cross section image storage section 32, and the reference table linking the EDS map and the etching rate together may be referred to from the etching rate storage section 33.

Then, the irradiation condition generation section 34 makes the etching rate map of the cross section 42s by comparing the brightness or the shading of the read SEM image with the reference table of the etching rate storage section 33 (S3: etching rate map creation).

Incidentally, in a case where the EDS detector 18 is provided as the cross section information obtaining means 19, the irradiation condition generation section 34 may create the etching rate map of the cross section 42s by comparing the read EDS map with the reference table of the etching rate storage section 33.

For example, if the cross section 42s of the sample S is formed by using the focused ion beam 21 using Ga as an ion species, a damaged layer caused by the collision of Ga ions is formed on the cross section 42s. Such a damaged layer is different in etching rate, compared to an undamaged area in the cross section 42s.

In a case where the EDS detector 18 is provided as the cross section information obtaining means 19, an etching rate map of the cross section 42s may be created with assuming the damaged layer due to Ga ions based on a Ga signal of an EDS image obtained by the EDS detector 18. That is, the etching rate map may be created such that an etching rate for a damaged layer is higher than that for an area without damage, with assuming a portion where more than a predetermined amount of residual Ga is present as the damaged layer.

Incidentally, with respect to the etching rate map, at least one of the etching rate map based on the SEM image and the etching rate map based on the EDS map may be created. If plural kinds of etching rate maps are created and combined, it is possible to improve the accuracy of the etching rate map of the cross section.

Then, the irradiation condition generation section 34 reads data of the irradiation interval and the irradiation time which are the irradiation conditions of the focused ion beam necessary for processing for each etching rate, from the processing condition storage section 31. Then, the irradiation conditions of the focused ion beam necessary to uniformly etch the entirety of the cross section 42s are generated based on the created etching rate map of the cross section 42s (S4: irradiation condition generation process). Such irradiation conditions represent the irradiation interval and the irradiation time of the focused ion beam necessary for etching according to the hardness for each micro-region of the cross section 42s.

Incidentally, in a case of making the irradiation intensity of the focused ion beam constant, such an irradiation condition is data representing the irradiation time for each micro-region of the cross section 42s. Further, in a case of making the irradiation time of the focused ion beam constant, such an irradiation condition is data representing the irradiation interval for each micro-region of the cross section 42s.

Next, the cross section processing control section 35 reads the irradiation conditions of the focused ion beam generated in the irradiation condition generation section 34. Then, the etching of the processing area 43 is performed while variably controlling the irradiation interval or the irradiation time of the focused ion beam 21 based on the irradiation conditions (S5: cross section processing process).

FIGS. 5A and 5B are explanatory diagrams showing an example of the etching of the sample. Incidentally, in the top views of FIGS. 5A and 5B, in order to make the irradiation of the focused ion beam easy to understand, each of areas E1 and E2 shows an internal structure in a depth direction and is not for showing a state of being exposed at a surface.

In the example shown in FIGS. 5A and 5B, the irradiation interval of the focused ion beam is variably controlled according to the etching rate of each of a plurality of materials configuring the sample S.

For example, at a cross section Sf of the sample S shown in FIG. 5A, the area E1 made of silicon and the area E2 made of tungsten inserted into the silicon are exposed. In a case of performing etching with the focused ion beam 21, in raster scan in which the irradiation intensity or the irradiation density of the focused ion beam 21 is made uniform, the area E2 made of tungsten having higher hardness than silicon has a low etching rate compared to the area E1, and thus curtaining occurs in this portion, whereby concaves and convexes are formed on a cross section formed by etching.

In contrast, in the cross section processing method according to the present invention, etching is performed in raster scan (line scan) while variably controlling the irradiation interval, the irradiation time, or the like of the focused ion beam (vector scan) in the course of line scanning according to an etching map of the cross section Sf created based on cross section information by an SEM image obtained in advance. For example, as shown in FIG. 5B, in the area E2 made of tungsten having higher hardness than silicon, the irradiation interval of the focused ion beam 21 in the course of line scanning is controlled so as to become closer than in the area E1 made of silicon. In this way, the cross section Sf is uniformly etched as a whole, and a cross section (an observation surface) which is exposed after the etching becomes substantially a flat surface with very few concaves and convexes.

As described above, if the etching of the processing area 43 is performed while variably controlling the irradiation interval of the focused ion beam 21, the cross section 43s being substantially flat and with very few concaves and convexes is obtained.

Here, the SEM image of the cross section 43s is formed by irradiating the cross section 43s formed by slicing with the electron beam 22 again. Then, the etching map of the cross section 43s is made based on the SEM image of the cross section 43s. Then, the irradiation condition representing the irradiation interval, the irradiation time, or the like of the focused ion beam necessary to uniformly etch the next processing area 44 regardless of a difference in the hardness of a material is generated.

Then, the etching of the processing area 44 is performed while variably controlling the irradiation interval of the focused ion beam based on the irradiation conditions for processing the processing area 44. In a case where the cross section of the processing area 44 is at the formation planned position R of the observation surface, the cross section is set as the observation surface 44s (S6: processing termination determination). In this way, the observation surface 44s being flat with very few concaves and convexes is formed. The observation surface 44s formed in this way has no concaves and convexes due to a difference in the hardness of a material and the formation of the curtaining due to a material having high hardness is also suppressed, and therefore, for example, in the case of a thin sample at the time of TEM observation, it becomes possible to obtain a clear observation image with an extremely high degree of accuracy.

(Another Embodiment of Cross Section Processing Method)

Figure 6A:
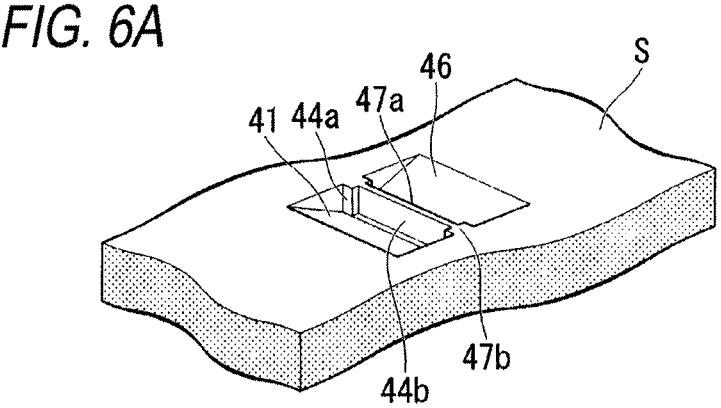
FIGS. 6A and 6B are explanatory diagrams showing a state of performing finish processing on a thin section of a sample by cross section processing.
Figure 6B:
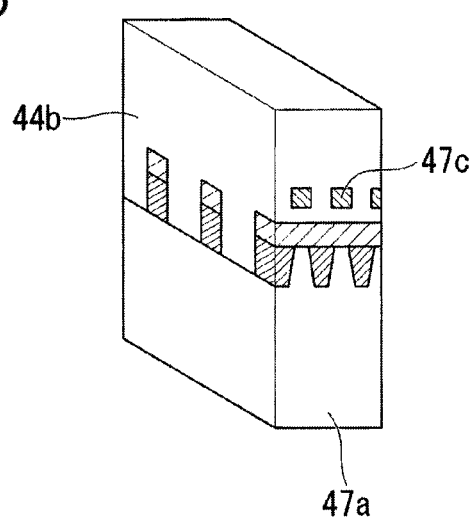

FIGS. 6A and 6B are explanatory diagrams showing a state of performing finish processing on a thin section of a sample by cross section processing, in which FIG. 6A shows the entire sample and FIG. 6B shows a portion of the thin section in an enlarged manner.

In a case of creating a thin section of a sample for TEM observation, the flatness of a cross section is important. In addition, by performing finish processing of reducing a film thickness so as to obtain a thin section which includes only a desired observation target (for example, a single device structure (a device structure 47*c* of FIG. 6B) to which attention is paid), it is possible to realize accurate TEM observation of a desired observation target. For example, in a recent miniaturized device, it is necessary to form a thin section having a film thickness of less than or equal to 50 nm and in particular, of several tens of nm.

For this reason, finish processing is performed by using a focused ion beam so as to further thin the thin section 47 obtained by the cross section processing method shown in FIG. 3D.

In FIGS. 6A and 6B, reference numeral 47*a* denotes a finish-processed thin section obtained by further thinning the thin section 47 shown in FIG. 3D by finish processing, and reference numeral 47*b* denotes an area on which finish processing has not been performed (that is, a portion still having the same thickness as the thin section 47 shown in FIG. 3D). Finish processing is performed such that only one device structure 47*c* eventually remains within the thickness of the finish-processed thin section 47*a*.

In such finish processing, EDS measurement is performed and the film thickness of a thin section is measured from signal intensity of EDS. When irradiating a cross section of the thin section with an electron beam for performing the EDS measurement, in a case where the film thickness of the thin section is small (for example, less than or equal to about 100 nm), a portion of the electron beam transmits through the thin section or the amount of the thin section which emits X-rays is reduced, and therefore, an EDS signal becomes weak. A film thickness is measured by using the correlation between the film thickness of such a thin section and the EDS signal.

In the measurement of the film thickness of the thin section, calibration data in which the relationship between the signal intensity of EDS and the remaining film thickness is examined by using a standard sample in which the size of the device structure 47*c* is already known is obtained in advance, and the calibration data is compared with the signal intensity of EDS of a cross section 44*b*. Alternatively, a film thickness may be determined by the comparison of EDS signals of an area 44*a* having a thickness through which an electron beam does not transmit and the measurement area (cross section) 44*b*.

Also in such finish processing, as in the embodiment shown in FIGS. 3A to 3D, a film thickness is measured while performing etching by variably controlling an irradiation interval, irradiation time, or the like (performing vector scan) in order to control a dose amount (an injection amount of electrons per unit area) of a focused ion beam, and when a thin section has reached a target film thickness, finish processing is ended. In this way, it is possible to form, for example, a thin section having a film thickness which includes only one device structure 47*c* to which attention is paid.

Since a thin section having a flat cross section can be made by such finish processing, it is possible to obtain an accurate TEM image in TEM observation. Further, the film thickness of a flat cross section is measured during finish processing and an ending point of the finish processing is detected, and therefore, a difference does not occur in an etching rate even in a sample which includes materials having different hardness, and it is possible to terminate the finish processing at a desired film thickness without making a mistake in film thickness detection.

Incidentally, in the above-described finish processing, a configuration can be made in which a signal based on transmission electrons, reflected electrons, or secondary electrons besides the EDS measurement is detected and a film thickness is measured while performing etching by controlling a dose amount of a focused ion beam from the signal.

As a method of measuring the film thickness of a thin section, for example, a technique disclosed in WO06/073063 can be used. That is, it is also possible to detect signals of transmission electrons, reflected electrons, or secondary electrons of the area 44*a* having a thickness through which an electron beam does not transmit and the measurement area 44*b* while performing etching by controlling a dose amount of a focused ion beam based on a signal of transmission electrons, reflected electrons, or secondary electrons of the measurement area 44*b* and to measure a film thickness.

The cross section processing apparatus and the cross section processing method according to the present invention have been described in detail above. However, the present invention is not limited to these embodiments unless otherwise specified.

In the above-described embodiments, an example has been shown in which the formation procedure of the cross sections is automatically performed. However, a configuration is also acceptable in which an operator performs etching while manually variably controlling the current value of the focused ion beam according to, for example, the shading of the SEM image of a cross section or the material distribution of the EDS map.

In the above-described embodiments, the irradiation conditions of the focused ion beam are generated according to the etching map created by the SEM image. However, in a configuration in which the EDS detector or the EBSD detector is provided as the cross section information obtaining means, the irradiation conditions of the focused ion beam may be generated according to the EDS map or the EBSD map.

In the above-described embodiments, the slicing and the cross section observation are repeated in a step-by-step manner until the observation surface is exposed. However, a configuration is also acceptable in which slicing is performed on an objective observation surface by single etching. In this case, the obtaining an SEM image by cross section observation is performed only once at the beginning.

As a method of eliminating a difference in etching rate due to a difference in hardness, the irradiation interval and the irradiation time of the focused ion beam are cited. However, these may be variably controlled individually, or, variable control of a combination of the two may also be performed.

What is claimed is:
1. A cross section processing method of performing processing of a cross section of a sample by irradiating the sample with a focused ion beam, the method comprising:
   forming a processing groove having a slope shape, in which a depth from a surface of the sample gradually increases as it advances in a processing direction, by etching by applying the focused ion beam to a vicinity of a formation planned position of an observation surface of the sample;
   slicing a processing area of the sample at a slice interval along the processing direction by etching by applying the focused ion beam to a cross section of the processing groove;
   obtaining cross section information of a cross section after the slicing; and etching the cross section after the slicing; by scanning the focused ion beam in a scanning direction while varying the density of an irradiation amount of the focused ion beam along the scanning direction, based on an etching rate map of the obtained cross section information of the cross section after the slicing, so as to form a substantially flat cross section.

2. The cross section processing method according to claim 1, wherein the varying the density of an irradiation amount of the focused ion beam comprises variably controlling at least one of an irradiation interval and irradiation time of the focused ion beam.

3. The cross section processing method according to claim 1, wherein the cross section information is contrast of the cross section or distribution of substances configuring the cross section.

4. The cross section processing method according to claim 1, wherein the etching rate map of the cross section is created based on contrast of the cross section or distribution of substances configuring the cross section.

5. The cross section processing method according to claim 1, wherein the obtaining cross section information comprises obtaining an SEM image of the cross section of the sample.

6. The cross section processing method according to claim 1, wherein the obtaining cross section information comprises performing EDS measurement or EBSD measurement of the cross section.

7. The cross section processing method according to claim 6, wherein the cross section information comprises information on an ion species of the focused ion beam measured by EDS measurement or EBSD measurement of the cross section.

8. The cross section processing method according to claim 1,
wherein the slicing a processing area of the sample is performed in a step-by-step manner until reaching an observation surface position having been set in advance, and
wherein the obtaining cross section information is performed at each step.

9. The cross section processing method according to claim 1, further comprising:
an irradiation condition generation process of generating irradiation conditions of the focused ion beam to be applied to the cross section based on the cross section information.

10. The cross section processing method according to claim 1,
wherein the obtaining cross section information comprises obtaining the cross section information based on EDS measurement or EBSD measurement of the cross section, and
wherein the method further comprises forming a thin section of the sample by performing processing of a cross section of one side and a cross section on the other side of the sample based on the obtained cross section information.

11. The cross section processing method according to claim 1,
wherein the obtaining cross section information comprises obtaining the cross section information based on transmission electrons, reflected electrons, or secondary electrons, and
wherein the method further comprises forming a thin section of the sample by performing processing of a cross section on one side and a cross section on the other side of the sample based on the obtained cross section information.

12. A cross section processing apparatus comprising:
a sample stage configured to place a sample thereon;
a focused ion beam column configured to irradiate and line scan the sample with a focused ion beam;
an electron beam column configured to irradiate the sample with an electron beam; and
a control section configured to control the cross section processing apparatus to perform:
a cross section information obtaining process of obtaining cross section information of the sample; and
a cross section processing process of forming an observation surface of the sample by performing etching of the cross section by irradiating and line scanning the sample with the focused ion beam while varying an irradiation amount of the focused ion beam in the course of line scanning, based on an etching rate map of the obtained cross section information, to form a substantially flat cross section observation surface.

13. The cross section processing apparatus according to claim 12, wherein varying the irradiation amount comprises varying the irradiation interval of the focused ion beam in the course of line scanning.

14. The cross section processing apparatus according to claim 12, wherein varying the irradiation amount comprises varying the irradiation time of the focused ion beam during the course of line scanning.

15. A cross section processing apparatus comprising:
a sample stage configured to place a sample thereon;
a focused ion beam column configured to irradiate and line scan the sample with a focused ion beam;
an electron beam column configured to irradiate the sample with an electron beam; and
a control section configured to control the cross section processing apparatus to perform a cross section processing process of forming an observation surface of the sample, the cross section processing process comprising:
(1) forming a processing groove having a slope shape, in which a depth from a surface of the sample gradually increases as it advances in a processing direction, by etching by applying the focused ion beam to a vicinity of a formation planned position of an observation surface of the sample;
(2) slicing a processing area of the sample at a slice interval along the processing direction by etching by applying the focused ion beam to a cross section of the processing groove;
(3) obtaining cross section information of a cross section after the slicing; and
(4) etching the cross section after the slicing by scanning the focused ion beam in a scanning direction while varying the density of an irradiation amount of the focused ion beam along the scanning direction, based on an etching rate map of the obtained cross section information of the cross section after the slicing, so as to form a substantially flat cross section.

16. The cross section processing apparatus according to claim 15, wherein the cross section processing process further comprises:
(5) determining whether the etched cross section reaches the formation planned position;
(6) when it is determined that the etched cross section does not reach the formation planned position, repeating (2) to (5); and (7) when it is determined that the etched cross section reaches the formation planned position, setting the etched cross section as the observation surface.

17. The cross section processing apparatus according to claim 15, further comprising:
a secondary electron detector configured to detect secondary electrons generated from the sample by being irradiated with the electron beam,
wherein the obtaining cross section information comprises:
irradiating the cross section after the slicing with the electron beam; and
obtaining a scanning electron microscope (SEM) image of the cross section after the slicing based on the secondary electrons generated from the cross section after the slicing.

18. The cross section processing apparatus according to claim 17,
wherein the obtaining cross section information further comprises:
generating an etching rate map of the cross section after the slicing based on the obtained SEM image; and
generating an irradiation condition of the focused ion beam based on the generated etching rate map, and
wherein the etching of the cross section after the slicing comprises etching the cross section after the slicing by being irradiated with the focused ion beam while varying an irradiation amount of the focused ion beam, based on the generated irradiation condition.

* * * * *